United States Patent
Rajendran et al.

(10) Patent No.: US 11,828,283 B2
(45) Date of Patent: Nov. 28, 2023

(54) PUMP ASSEMBLY AND A WOUND THERAPY APPARATUS

(71) Applicant: CONVATEC LIMITED, Flintshire (GB)

(72) Inventors: Ganesh Rajendran, Banagalore (IN); Greeshma Girijakumari, Banagalore (IN); S Lakshmana, Banagalore (IN); Ankur Kodavanti, Banagalore (IN); Praveen Kadni, Banagalore (IN)

(73) Assignee: ConvaTec Limited, Flintshire (GB)

( * ) Notice: Subject to any disclaimer, the term of this patent is extended or adjusted under 35 U.S.C. 154(b) by 0 days.

(21) Appl. No.: 17/160,670

(22) Filed: Jan. 28, 2021

(65) Prior Publication Data

US 2021/0228785 A1    Jul. 29, 2021

Related U.S. Application Data

(63) Continuation of application No. PCT/GB2021/050194, filed on Jan. 28, 2021.

(30) Foreign Application Priority Data

Jan. 29, 2020    (GB) .................................... 2001214

(51) Int. Cl.
*F04B 7/00*    (2006.01)
*A61M 1/00*    (2006.01)

(52) U.S. Cl.
CPC ............. *F04B 7/0076* (2013.01); *A61M 1/94* (2021.05); *A61M 2205/0272* (2013.01)

(58) Field of Classification Search
CPC ...... F04B 17/003; F04B 43/04; F04B 43/043; F04B 43/046; F04B 43/09; F04B 43/095;

(Continued)

(56) References Cited

U.S. PATENT DOCUMENTS 4,058,123 A * 11/1977 May ..................... A61M 1/0058
                                                      604/35
5,542,821 A *  8/1996 Dugan .................. F04B 43/043
                                                      417/322

(Continued)

FOREIGN PATENT DOCUMENTS

EP        3347068 B1    7/2021
EP        3592313 B1    7/2021

(Continued)

OTHER PUBLICATIONS

Examination Opinion; Intellectual Property Office of the United Kingdom; Patent Application No. GB2001214.2; dated Jul. 9, 2020; 2 pages.

(Continued)

*Primary Examiner* — Erich G Herbermann
*Assistant Examiner* — Seth Han
(74) *Attorney, Agent, or Firm* — Taft Stettinius & Hollister LLP; Ryan O. White; Derek B. Lavender (57) ABSTRACT

A pressure gradient wound therapy apparatus (50) including a pump assembly (10). The pump assembly (10) includes a diaphragm (12) comprising a magnetic material (16), an electromagnetic actuator (18) switchable between two or more operational states and a valve arrangement (24) including an inlet valve (26) and an outlet valve (28) for the introduction and/or removal of fluid into a fluid chamber (30) of the pump assembly (10). The actuator (18) is configured to move the diaphragm (12) with respect to the actuator (18) between a first position corresponding to a first operational state of the actuator (18) and a second position corresponding to the second operational state of the actuator (18).

18 Claims, 4 Drawing Sheets

(58) Field of Classification Search
CPC ...... F04B 7/0076; F04B 45/067; F04B 45/00;
F04B 45/04; F04B 45/06; F04B 45/047;
A61M 1/90; A61M 1/91; A61M 1/96;
A61M 1/966; A61M 1/82; A61M 1/94;
A61M 1/92
USPC ......................................................... 604/141
See application file for complete search history.

(56) References Cited

U.S. PATENT DOCUMENTS

| | | | |
|---|---|---|---|
| 11,026,847 B2 | 6/2021 | Piotrowski et al. | |
| 11,173,240 B2 | 11/2021 | Askem et al. | |
| 11,197,953 B2 | 12/2021 | Heaton et al. | |
| 11,364,334 B2 | 6/2022 | Long et al. | |
| 11,395,870 B2 | 7/2022 | Askem et al. | |
| 2002/0098122 A1* | 7/2002 | Singh | B01L 3/5027 422/400 |
| 2005/0004534 A1* | 1/2005 | Lockwood | A61M 1/964 604/304 |
| 2006/0013710 A1 | 1/2006 | Lee | |
| 2012/0083759 A1* | 4/2012 | Kirkpatrick | F04B 43/14 604/153 |
| 2013/0331823 A1* | 12/2013 | Askem | F04B 53/10 417/44.1 |
| 2015/0250931 A1* | 9/2015 | Bharti | A61M 1/90 604/319 |
| 2017/0209641 A1* | 7/2017 | Mercer | A61M 3/0283 |
| 2021/0187171 A1 | 6/2021 | Collinson et al. | |
| 2021/0244570 A1 | 8/2021 | Askem et al. | |
| 2021/0260271 A1 | 8/2021 | Locke et al. | |
| 2021/0401358 A1 | 8/2021 | Askem et al. | |
| 2021/0290837 A1 | 9/2021 | Brandolini et al. | |
| 2021/0322666 A1 | 10/2021 | Greener | |
| 2021/0338489 A1 | 11/2021 | Hunt et al. | |
| 2021/0361854 A1 | 11/2021 | Askem et al. | |
| 2022/0062526 A1 | 3/2022 | Teaton et al. | |
| 2022/0080105 A1 | 3/2022 | Askem et al. | |
| 2022/0133978 A1 | 5/2022 | Askem et al. | |
| 2022/0176032 A1 | 6/2022 | Randolph et al. | |

FOREIGN PATENT DOCUMENTS

| | | |
|---|---|---|
| EP | 3452130 B1 | 12/2021 |
| EP | 3454917 B1 | 4/2022 |
| GB | 2588482 B | 4/2021 |
| GB | 2589503 B | 6/2021 |
| WO | 2004037334 A1 | 5/2004 |
| WO | 2009124100 A1 | 10/2009 |
| WO | 2011146535 A1 | 11/2011 |

OTHER PUBLICATIONS

International Search Report; European Patent Office; International Application No. PCT/GB2021/050194; dated Jun. 15, 2021; 3 pages.
Written Opinion of the International Searching Authority; European Patent Office; International Application No. PCT/GB2021/050194; dated Jun. 15, 2021; 5 pages.
Written Opinion of the International Searching Authority; European Patent Office; International Application No. PCT/GB2021/050194; dated Jun. 15, 2022; 5 pages.

* cited by examiner

PUMP ASSEMBLY AND A WOUND THERAPY APPARATUS

CROSS-REFERENCE TO RELATED APPLICATIONS

The present application is a continuation of International Application No. PCT/GB2021/050194 filed Jan. 28, 2021 and which claims the benefit of GB2001214.2 filed Jan. 29, 2020, the contents of which are hereby incorporated herein in their entirety.

TECHNICAL FIELD OF THE INVENTION

The present invention relates to a pump assembly and a wound therapy apparatus, and in particular to a pump assembly for a pressure gradient wound therapy apparatus and an apparatus comprising the same.

BACKGROUND TO THE INVENTION

Pressure gradient wound therapy (positive or negative) is a known way of treating various wound types. Typically, this involves applying a pressure differential between a sealed region of a wound dressing and the surrounding environment to assist with healing the wound, e.g. through removal of oedema, increasing blood flow, mechanical contraction of the wound, increasing formation of granulation tissue and/or active removal of excess exudate from the wound. Wound therapy of this type is particularly effective for the treatment of open traumatic, non-traumatic and chronic wounds.

The pressure differential is applied through the introduction or removal of gas from within the sealed region of the wound dressing. Such systems typically employ a pump, at least initially, to achieve the desired pressure level within the wound dressing. The pump may be operated throughout, or periodically throughout the treatment, or may be applied initially before relying on the seal between the wound dressing and the surrounding environment to maintain the desired pressure level during treatment. Typically, diaphragm or membrane pumps are used which utilise the reciprocating action of a diaphragm (and suitable valve arrangement) to pump the gas into or out of the wound dressing.

More recently, systems have been developed whereby movement of the diaphragm may be controlled using an electromagnet suitably mounted to the diaphragm—akin to a voice coil/speaker arrangement. In such systems, a permanent magnet is used to provide a constant magnetic field with which the electromagnet may interact. Specifically, interaction between the constant magnetic field and a magnetic field induced by the electromagnet is used to cause corresponding movement of the diaphragm. The direction of movement is controlled by periodically switching the orientation of the field induced by the electromagnet causing the diaphragm to move back and forth to provide the required pumping action.

Advantageously, such systems reduce the number of components which are required to be physically coupled to one another, thereby reducing friction losses in the system and improving overall efficiency. However, a strong permanent magnet must be used in order to provide the necessary constant magnetic field to move the electromagnet and diaphragm as required. This is problematic from a weight and size point of view, leading to pump assemblies which can be bulky and heavy.

It would therefore be advantageous to provide a pump assembly for a wound therapy apparatus which does not suffer such drawbacks.

It is therefore an aim of an embodiment or embodiments of the invention to overcome or at least partially mitigate the problems associated with the prior art.

SUMMARY OF THE INVENTION

According to an aspect of the invention there is provided a pressure gradient wound therapy apparatus comprising a pump assembly, the pump assembly comprising: a diaphragm, an electromagnetic actuator and a valve arrangement; wherein the actuator is fixed in position within the apparatus and is spatially separated from the diaphragm; and the actuator is configured to induce a magnetic field in at least one operational state for moving the diaphragm with respect to the actuator between a first position and a second position.

According to an aspect of the invention there is provided a pressure gradient wound therapy apparatus comprising a pump assembly, the pump assembly comprising: a diaphragm comprising a magnetic material; an electromagnetic actuator switchable between two or more operational states, at least one of which comprises a state in which the actuator induces a magnetic field for moving the diaphragm; and a valve arrangement including an inlet valve and an outlet valve configured to allow for the introduction and/or removal of fluid into a fluid chamber of the pump assembly; wherein the actuator is fixed in position within the apparatus and is spatially separated from the diaphragm; and the actuator is configured to move the diaphragm with respect to the actuator between a first position corresponding to a first operational state of the actuator and a second position corresponding to the second operational state of the actuator.

Advantageously, having a fixed electromagnet removes the need to provide a field strong enough to move the electromagnet itself. This allows for the size of any permanent magnet to be significantly reduced. In the present invention, the improvements realised are such that where a permanent magnet is included, it can be provided in the form of a magnetic material forming part (or all) of the diaphragm. This reduces the size and weight of the pump assembly as a whole. In some instances, it may be beneficial to provide a system wherein the pump assembly is integrated with a wound dressing itself. Clearly, having a large, heavy pump would be unsuitable for such applications and therefore a reduction in the size and weight of the pump assembly would be advantageous. Further, in this way, a wound therapy apparatus can be provided whereby the only necessary moving component is the diaphragm. This reduction of the number of moving parts further realises improvements in efficiency and noise, for example.

When used herein and throughout the specification the term "pressure gradient wound therapy apparatus" is intended to cover a wound therapy apparatus wherein a pressure differential (either positive or negative) is applied between a sealed region of the wound dressing and the surrounding environment.

As used herein, negative pressure wound therapy is a therapeutic technique using a suction dressing to remove excess exudation and promote healing in acute or chronic wounds. A vacuum of −50 to −200 mm Hg, or −75 to −150 mm Hg may be applied with typical negative pressure of −80 to −130 mm Hg, −100 to −130 mm Hg, or often about −125 mm Hg being applied to a wound.

For positive pressure wound therapy, a net positive pressure is applied to the wound, which may include providing simultaneous aspiration and irrigation of the wound. Positive pressure wound therapy may be carried out at a positive pressure of up to 50% atm., typically at a low positive pressure of up to 20% atm., more usually up to 10% atm. at the wound. Positive pressure wound therapy is known and referred to in US20180140755.

When used herein and throughout the specification, the term "spatially separated" may mean an arrangement where the actuator and the diaphragm are not connected, coupled or otherwise attached in any way—e.g. they have an air gap therebetween. Rather, with the actuator fixed in position with respect to the apparatus, the diaphragm is free to move with respect to the actuator without the actuator physically acting on the diaphragm to move the diaphragm between the first and second positions. Rather, the diaphragm is moved under the influence of a magnetic field induced by the actuator, or equally the removal of an induced magnetic field as is described herein.

Optional features set out below may apply to any aspect of the invention.

In embodiments, the apparatus comprises a negative pressure wound therapy apparatus. In such embodiments, the pump assembly may be operable in use to remove gas from within an applied wound dressing to create the pressure differential between the wound dressing and the surrounding environment. In other embodiments, the apparatus comprises a positive pressure wound therapy apparatus. In such embodiments, the pump assembly may be operable to introduce gas into the applied wound dressing to create the pressure differential between the wound dressing and the surrounding environment.

The actuator may be configured to move the diaphragm towards or away from the actuator when in the first or second operational state. For example, in some embodiments the actuator is configured such that upon switching between the first operational state and the second operational state the actuator is configured to move the diaphragm towards or away from the actuator.

In embodiments, in switching from the first operational state to the second operational state the actuator is configured to move the diaphragm in a first direction from the first position towards the second position. The first direction may be away from the actuator. In some embodiments in switching from the second operational state to the first operational state the actuator is configured to move the diaphragm in a second direction from the second position to the first position. The second direction may be towards the actuator.

In some embodiments the electromagnetic actuator is operable to induce a first magnetic field in the first operational state. In such embodiments, the electromagnetic actuator may be configured to induce a second magnetic field in the second operational state. The first magnetic field and second magnetic field may be opposing magnetic fields. For example, the first and second magnetic fields may act in opposing directions. In embodiments, the actuator is configured to move the diaphragm in a first direction to the first position under the influence of the first magnetic field, and to move the diaphragm in a second direction towards the second position under the influence of the second magnetic field.

Alternatively, the electromagnetic actuator may be operable to induce a magnetic field in the first operational state, only. For example, the actuator may be configured to move the diaphragm in a first direction towards the first position under the influence of the magnetic field. The actuator may be configured such that the diaphragm moves in a second direction towards the second position in the absence of the magnetic field. This movement may be provided by a biasing force provided by or applied to the diaphragm.

Accordingly, one particularly preferred embodiment provides a pressure gradient wound therapy apparatus comprising a pump assembly, the pump assembly comprising: a diaphragm comprising a magnetic material; an electromagnetic actuator switchable between two or more operational states, at least one of which comprises a state in which the actuator induces a magnetic field for moving the diaphragm; and a valve arrangement including an inlet valve and an outlet valve configured to allow for the introduction and/or removal of fluid into a fluid chamber of the pump assembly; wherein the actuator is fixed in position within the apparatus and is spatially separated from the diaphragm; and the actuator is configured to move the diaphragm with respect to the actuator between a first position corresponding to a first operational state of the actuator and a second position corresponding to the second operational state of the actuator; wherein the electromagnetic actuator is operable to induce a magnetic field in the first operational state, only.

Another particularly preferred embodiment provides a pressure gradient wound therapy apparatus comprising a pump assembly, the pump assembly comprising: a diaphragm comprising a magnetic material; an electromagnetic actuator switchable between two or more operational states, at least one of which comprises a state in which the actuator induces a magnetic field for moving the diaphragm; and a valve arrangement including an inlet valve and an outlet valve configured to allow for the introduction and/or removal of fluid into a fluid chamber of the pump assembly; wherein the actuator is fixed in position within the apparatus and is spatially separated from the diaphragm; and the actuator is configured to move the diaphragm with respect to the actuator between a first position corresponding to a first operational state of the actuator and a second position corresponding to the second operational state of the actuator; wherein the electromagnetic actuator is operable to induce a magnetic field in the first operational state, only; wherein the actuator is configured to move the diaphragm in a first direction towards the first position under the influence of the magnetic field; and wherein the actuator is configured such that the diaphragm moves in a second direction towards the second position in the absence of the magnetic field.

Another particularly preferred embodiment provides a pressure gradient wound therapy apparatus comprising a pump assembly, the pump assembly comprising: a diaphragm comprising a magnetic material; an electromagnetic actuator switchable between two or more operational states, at least one of which comprises a state in which the actuator induces a magnetic field for moving the diaphragm; and a valve arrangement including an inlet valve and an outlet valve configured to allow for the introduction and/or removal of fluid into a fluid chamber of the pump assembly; wherein the actuator is fixed in position within the apparatus and is spatially separated from the diaphragm; and the actuator is configured to move the diaphragm with respect to the actuator between a first position corresponding to a first operational state of the actuator and a second position corresponding to the second operational state of the actuator; wherein the electromagnetic actuator is operable to induce a magnetic field in the first operational state, only; wherein the actuator is configured to move the diaphragm in a first direction towards the first position under the influence of the magnetic field; wherein the actuator is configured such that the diaphragm moves in a second direction towards the second position in the absence of the magnetic field; and wherein movement of the diaphragm in the second direction is provided by a biasing force provided by or applied to the diaphragm.

In embodiments the apparatus may be configured such that a biasing force is provided which acts to bias the diaphragm to a "resting" position. The resting position may correspond to the first position or to the second position. In other embodiments the resting position may correspond to a third position. The third position may be an intermediary position between the first and second positions.

In embodiments, the biasing force may be provided by the diaphragm itself. For example, in some embodiments the diaphragm may comprise a flexible and/or resilient material, such as a polymeric material or a flexible metal material, for example, configured to provide a biasing force upon extension or compression of the diaphragm, e.g. through deflection of the diaphragm under the operation of the actuator. In other embodiments the apparatus may comprise a biasing member configured to apply the biasing force to the diaphragm.

The magnetic material of the diaphragm may comprise a soft magnet or a hard magnet. The magnetic material of the diaphragm may comprise a permanent magnetic material. A hard/permanent magnet has the advantage that it can respond to the magnetic field produced by the actuator by both attraction and repulsion, whereas a soft magnetic material may only respond by attraction.

The magnetic material of the diaphragm may comprise a ferromagnetic or ferrimagnetic material. In embodiments the diaphragm may comprise aluminium, iron, cobalt, nickel, manganese, zinc or an alloy containing the same. In embodiments, the diaphragm may comprise a rare-earth element such as neodymium or samarium, for example, or alloys containing the same.

In some embodiments the diaphragm may be formed of a non-magnetic material. In such embodiments, the magnetic material of the diaphragm may comprise a magnetic component attached, coupled or otherwise fixed to the non-magnetic material. The magnetic component may comprise a thin film layer or coating. In embodiments the diaphragm comprises a magnetic paint applied to the non-magnetic material.

In some embodiments the electromagnetic actuator may be configured to periodically switch between the first and second operational states. In this way, the actuator may be operable to cause a pumping action of the diaphragm, periodically moving between the first and second positions. In use, periodically switching between the first and second operational states may be performed through periodic switching of the direction of current supplied to the actuator, or through periodic switching of the supply current on and off. The electromagnetic actuator may be operable to periodically switch between first and second operational states at a rate of up to 500 Hz, up to 1000 Hz or up to 2000 Hz, and/or it may be operable to periodically switch between first and second operational states at a rate of at least 500 Hz, or at least 1000 Hz, or at least 1500 Hz, or at least 2000 Hz, for example.

The apparatus may be configured to achieve a pressure differential between the wound dressing and the environment of up to 200 mHg. In particular, the apparatus may be configured to achieve a vacuum of −50 to −200 mm Hg; −75 to −150 mm Hg; −80 to −130 mm Hg; −100 to −130 mm Hg, or about −125 mm Hg. The electromagnetic actuator may be required to operate (e.g. to cause periodic movement of the diaphragm) for a period of no more than 60 seconds, or no more than 30 seconds or no more than 15 s to achieve the desired pressure differential; and/or the electromagnetic actuator may be required to operate for more than 15 s, or more than 30 s, or more than 45 s, or more than 60 s to achieve the desired pressure differential.

In some embodiments the diaphragm is configured to translate between the first position and the second position—i.e. move in its entirety between the first and second positions. In some embodiments the diaphragm is configured to deflect between first second positions under the operation of the actuator. In such embodiments, the diaphragm may be fixed within the pump assembly and/or the apparatus as a whole. For example, in some embodiments the diaphragm may be fixed at its peripheral edge(s). The diaphragm may deflect between a concave shape and a convex shape. The first position may correspond to the concave shape and the second position may correspond to the convex shape.

The diaphragm may be configured to move (e.g. deflect) by up to 5 mm or by up to 10 mm, or by up to 20 mm; and/or it may be configured to move by at least 5 mm, or by at least 10 mm, or by at least 15 mm, or by at least 20 mm, for example.

The diaphragm may be configured such that movement thereof causes a corresponding volume change of the fluid chamber of up to 5 mm$^3$, or up to 10 mm$^3$, or up to 20 mm$^3$; and/or it may be configured to move by at least 5 mm$^3$, or at least 10 mm$^3$, or at least 15 mm$^3$, or at least 20 mm$^3$, for example.

The diaphragm may be substantially circular in shape. The (substantially) circular diaphragm may comprise a diameter of up to 25 mm, or up to 50 mm. or up to 100 mm; and/or it may comprise a diameter of; and/or it may comprise a diameter of at least 25 mm, or at least 50 mm, or at least 75 mm, or at least 100 mm, for example. In alternative embodiments the diaphragm may be substantially elliptical, square, rectangular or polygonal in shape. The diaphragm may comprise an irregular shape. In such embodiments the diaphragm may have a length and/or width in any of the ranges outlined above.

The wound therapy apparatus may comprise a wound dressing. The wound dressing may include a dressing body formed of an absorbent material which may be positioned in contact with a wound, in use. The dressing body may be configured to absorb exudate from the wound, aided by the action of the pump assembly. The dressing body may comprise an absorbent foam material, for example. The foam material may comprise a superabsorbent foam material. The dressing body may be formed of a hydrocolloid material which may gel in the presence of an exudate. The hydrocolloid material may comprise a layer or multiple layers of gelling fibres and absorbent materials. The outer surface of the dressing may be constructed of a thin film layer (e.g. a polyurethane) enabling moisture vapour to exit the dressing at an increased rate. This combination would allow the wound therapy apparatus to manage fluid without the need of a canister. This may be referred to as a "canister-less" or "canister free" system. In a variant, the wound dressing may be fluidly connected to a canister into which exudate removed from the wound may be withdrawn. The dressing may include an adhesive layer for providing a seal between the dressing and the user's skin, in use. The adhesive layer may define an interior region of the wound dressing.

The pump assembly may be fluidly connected to an interior region of the wound dressing, for introducing and/or removing gas from within the wound dressing to control the pressure therein. The pump assembly may be fluidly connected to the interior region of the wound dressing via a tube or conduit.

The inlet valve and outlet valve may preferably comprise one-way valves.

The wound dressing may have a thickness between 1 mm to 20 mm, or 2 mm to 10 mm, or 3 mm to 7 mm, for example. The wound dressing may be comprised of one or more layers including an outer cover layer, an absorbent layer, a gel-forming fibre, an adhesive layer, a wound contact layer, a distribution layer, and combinations thereof. The wound dressing may include one or more absorbent layer(s). The absorbent layer may be a foam or a superabsorbent. If foam is used, the foam may also act as a distribution layer. The wound dressing may comprise an outer cover layer and one or more absorbent layer(s) and a silicone gel wound contact layer. The wound dressing may comprise an outer cover layer and one or more absorbent layer(s) in combination with a gel-forming fibre. The gel-forming fibre typically is in direct contact with the wound, and thus no additional wound contact layer is required i.e., a silicone gel wound contact layer does not require a silicone gel layer.

Gel-forming fibres include hygroscopic fibres which upon the uptake of wound exudate become moist slippery or gelatinous. The gel forming fibres can be of the type which retain their structural integrity on absorption of exudate or can be of the type which lose their fibrous form and become an amorphous or structureless gel. The gel forming fibres are preferably sodium carboxymethylcellulose fibres, chemically modified cellulosic fibres, alkyl sulphonate modified cellulosic fibres such as those described in WO2012/061225, pectin fibres, alginate fibres, chitosan fibres, hyaluronic acid fibres, or other polysaccharide fibres or fibres derived from gums. The cellulosic fibres preferably have a degree of substitution of at least 0.05 carboxymethyl groups per glucose unit. The gel forming fibres preferably have an absorbency of at least 2 grams 0.9% saline solution per gram of fibre (as measured by the free swell method).

The gel forming fibres are preferably chemically modified cellulosic fibres in the form of a fabric and in particular carboxymethylated cellulose fibres as described in PCT WO00/01425 to Azko Nobel UK Ltd, and can be provided by a layer of gel forming fibres preferably located in a port of the cover layer or as a layer of fibres in a conduit of the wound dressing. When present in the conduit, the layer of fibres can also serve to keep the conduit open to the passage of fluid in the event that the conduit is kinked or otherwise restricted by being lain on or leaned on by the user. The carboxymethylated cellulosic fabrics preferably have a degree of substitution between 0.12 to 0.35 as measured by IR spectroscopy (as defined in WO00/01425) more preferably a degree of substitution of between 0.20 and 0.30 and are made by carboxymethylating a woven or non-woven cellulosic fabric such that the absorbency is increased. Particular preferred fabrics have an absorbency of between 10 g/g of sodium/calcium chloride as defined above to 30 g/g of sodium/calcium chloride as measured by the method described in BS EN 13726-1 (2002) "Test methods for primary wound dressings", section 3.2 "Free swell absorptive capacity". Particularly preferred fabrics have an absorbency of 15 g/g to 25 g/g and most preferred of 15 g/g to 20 g/g of sodium/calcium chloride as measured by the method defined above.

The cellulosic fabric preferably consists solely of cellulosic fibre but may contain a proportion of non-cellulosic textile fibre or gel forming fibre. The cellulosic fibre is of known kind and may comprise continuous filament yarn and/or staple fibre. The carboxymethylation is generally performed by contacting the fabric with an alkali and a carboxymethylating agent such a chloracetic acid in an aqueous system. The fabric is preferably of a non-woven type to reduce shedding in the wound on cutting the dressing. Preferably the fabric is hydroentangled and thus comprises a series of apertures on a microscopic scale.

Where present, the absorbent layer of the wound dressing is capable of absorbing exudate from the wound and allowing the passage of fluid through it. The absorbent layer can comprise any absorbent capable of absorbing exudate while allowing the passage of fluid through it, such as a foam, sponge or fibre-based material, preferably the absorbent layer is provided by gel forming fibres of the same type or of a different type as those discussed above. The gel-forming fibres are hygroscopic fibres which upon the uptake of wound exudate become moist slippery or gelatinous and thus reduce the tendency for the surrounding fibres to adhere to the wound. The gel forming fibres are preferably spun sodium carboxymethylcellulose fibres, chemically modified cellulosic fibres, alkyl sulphonate modified cellulosic fibres such as those described in WO2012/061225, pectin fibres, alginate fibres, chitosan fibres, hyaluronic acid fibres, or other polysaccharide fibres or fibres derived from gums. The cellulosic fibres preferably have a degree of substitution of at least 0.05 carboxymethyl groups per glucose unit and more preferably are lightly substituted so that the absorbency of the fibres is limited. The gel forming fibres preferably have an absorbency of at least 2 grams 0.9% saline solution per gram of fibre (as measured by the method described above) but less than 30 grams 0.9% saline solution per gram of fibre. The gel forming fibres are preferably carboxymethylated cellulose fibres as described in PCT WO00/01425 to Azko Nobel UK Ltd which describes lightly carboxymethylated cellulose fabrics. The gel forming fibres are preferably lightly carboxymethylated in order to reduce the tendency of the absorbent layer to gel block and block the pathway for fluid from the wound, e.g. through the absorbent layer, the port and to a distal end of the conduit.

Preferably the absorbent layer, where present, is provided with fenestrations to aid the application of negative pressure to the wound and maintain the pathway for fluid from the wound, through the absorbent layer. Typically, however, fenestrations are only provided in internal absorbent layers. External absorbent layers, including those in direct contact with the wound, generally do not have mechanically added fenestrations, however, they may include openings between the fibres.

Although the absorbent layer can be in direct contact with the wound, preferably the dressing comprises a wound contact layer, positioned between the wound and the absorbent layer. The wound contact layer may be capable of absorbing exudate from the wound and transmitting it to the absorbent layer. Like the absorbent layer, the wound contact layer may be capable of allowing the passage of fluid through it so that pressure (either positive or negative) may applied to the wound and the pathway for fluid/exudate from the wound to the distal end of the conduit may be maintained.

The wound contact layer may include gel-forming fibres (e.g. of the type discussed herein), or a silicone gel, for example.

Preferably the wound contact layer comprises gel-forming fibres. The gel-forming fibres may be the same or a similar type to those comprising the absorbent layer but the wound contact layer may be strengthened to increase its integrity and that of the dressing. For example, the wound contact layer may be of the type described in EP 1904011 and comprise gel-forming fibres in the form of a mat with lines of longitudinal stitching made of cellulose or nylon or polyolefin yarn to increase the integrity of the layer. Preferably the wound contact layer is porous to maintain the pathway for fluid/exudate from the wound to the distal end of the conduit.

An outer cover layer of the dressing is provided as a bacterial and viral barrier layer which preferably resists the ingress of liquid and air but allows moisture vapour transmission. In this way the outer cover layer enhances the overall fluid handling capacity of the dressing by allowing for the escape of moisture vapour through the cover while enabling the application of pressure (either positive or negative) to the wound. The outer cover layer is for instance a layer having a MVTR of at least 10,000 g m$^{-2}$ per 24 hours or in the range of from 10,000 gm$^{-2}$ to 50,000 g m$^{-2}$ per 24 hours measured by the method described in BS EN 13726-2 2002 "Test methods for primary wound dressings Part 2 Moisture vapour transmission rate of permeable film dressings". The cover layer may be in the form of a film of polyurethane, for example Epurex 912 T/129 manufactured by Covestro or Inspire 2350 manufactured by Coveris or Medifilm 426 manufactured by Mylan.

The cover layer can be provided with a port for connection to the conduit. The port is preferably located in the cover layer and overlies the absorbent layer towards the periphery of the absorbent layer so that it is not directly in vertical alignment with the centre of the dressing (or the wound when in use). This assists in the spread of exudate across the full extent of the absorbent layer.

The conduit of the dressing is preferably a transparent passageway secured to the outside of the cover layer at the proximal end of the conduit so as to surround the port in the cover layer from above. The conduit of the dressing may comprise a connector, at its distal end, for connecting the dressing to a source of pressure (either positive or negative), for example a pump. Preferably the connector is a luer lock to facilitate secure connection to the pump and to maintain the pressure within the wound dressing while the pump is temporarily disconnected. The connector preferably comprises a one-way lock to assist in the maintenance of the applied pressure. To resist collapse, the conduit may comprise an internal cylinder of nylon fibres to maintain openness of the conduit to fluid.

The dressing may further comprise a distribution layer, e.g., a pressure distribution layer, located between the absorbent layer and the outer cover layer which is gas and liquid permeable and particularly moisture vapour permeable and serves to aid access of exudate to a greater area of the absorbent layer by allowing it to spread under the distribution layer. The distribution layer also serves to even out the negative pressure applied to the wound over the whole dressing. The distribution layer preferably distributes exudate and negative pressure over the dressing. In this way, uptake of exudate by the absorbent layer is maximised before the exudate leaves the absorbent layer and activates the indicator means and the transfer of negative pressure to the wound is optimised. The distribution layer is preferably a foam layer such as a polyester foam of the type XD4200AS manufactured by Caligen or another suitable reticulated foam.

The dressing may also comprise additional optional layers such as an adhesive layer for adhering the dressing to the skin surrounding the wound to form a fluid tight seal. The adhesive layer may be applied to the side of dressing closest to the wound and may be provided with perforations to assist transport of exudate and fluid through the dressing. The adhesive layer may also be applied to any of the other layers to provide an island configuration such as to the cover layer.

According to another aspect of the invention there is provided a pump assembly, optionally for a pressure gradient wound therapy apparatus, comprising: a diaphragm, an electromagnetic actuator and a valve arrangement; wherein the actuator, in use, is fixed in position within the apparatus and is spatially separated from the diaphragm; and the actuator is configured to induce a magnetic field in at least one operational state for moving the diaphragm with respect to the actuator between a first position a second position.

According to a further aspect of the invention there is provided a pump assembly for a pressure gradient wound therapy apparatus, the pump assembly comprising: a diaphragm comprising a magnetic material; an electromagnetic actuator switchable between two or more operational states, at least one of which comprises a state in which the actuator induces a magnetic field for moving the diaphragm; and a valve arrangement including an inlet valve and an outlet valve configured to allow for the introduction and/or removal of fluid into a fluid chamber of the pump assembly; wherein the actuator, in use, is fixed in position within the apparatus and is spatially separated from the diaphragm; and the actuator is configured to move the diaphragm with respect to the actuator between a first position corresponding to a first operational state of the actuator and a second position corresponding to the second operational state of the actuator.

Definitions set out above, as well as optional features set out above in relation to the aspects of the invention concerning pressure gradient wound therapy apparatus, apply equally to these aspects of the invention concerning pump assemblies therefore. For example, in embodiments, the pump assembly comprises a pump assembly for a negative pressure wound therapy apparatus as outlined above, and the diaphragm is configured as discussed herein, e.g. to move in the directions outlined above when switching between operational states.

DETAILED DESCRIPTION OF THE INVENTION

In order that the invention may be more clearly understood one or more embodiments thereof will now be described, by way of example only, with reference to the accompanying drawings, of which.

Embodiments disclosed herein relate to apparatus and methods of treating a wound with reduced or positive pressure (typically negative pressure), including pump and wound dressing components and devices. The devices and components may include a wound overlay and packing materials, which may be collectively referred to interchangeably herein as "dressings" or "wound dressings".

As disclosed herein the present invention may comprise an apparatus for providing pressure gradient wound therapy to a wound, comprising: the technology disclosed herein, a wound dressing described herein; and a source of positive or negative pressure.

As used herein the expression "wound" may include an injury to living tissue may be caused by a cut, blow, or other impact, typically one in which the skin is cut or broken. A wound may be a chronic or acute injury. Acute wounds occur as a result of surgery or trauma. They move through the stages of healing within a predicted timeframe. Chronic wounds typically begin as acute wounds. The acute wound can become a chronic wound when it does not follow the healing stages resulting in a lengthened recovery. It is believed that the transition from acute to chronic wound can be due to a patient being immuno compromised.

Chronic wounds may include for example: venous ulcers (such as those that occur in the legs), which account for the majority of chronic wounds and mostly affect the elderly, diabetic ulcers (for example, foot or ankle ulcers), peripheral arterial disease, pressure ulcers, or epidermolysis bullosa (EB).

Examples of other wounds include, but are not limited to, abdominal wounds or other large or incisional wounds (either as a result of surgery, trauma, stemiotomies, fasciotomies, or other conditions), dehisced wounds, acute wounds, chronic wounds, subacute and dehisced wounds, traumatic wounds (such as from orthopaedic trauma), flaps and skin grafts, lacerations, abrasions, contusions, burns, diabetic ulcers, pressure ulcers, stoma, surgical wounds, trauma and venous ulcers, broken bones or the like.

Wounds may also include a deep tissue injury. Deep tissue injury is a term proposed by the National Pressure Ulcer Advisory Panel (NPUAP) to describe a unique form of pressure ulcers. These ulcers have been described by clinicians for many years with terms such as purple pressure ulcers, ulcers that are likely to deteriorate and bruises on bony prominences.

The technology disclosed can be used on an acute or chronic wound.

Wounds are believed to be more susceptible to infection under the following circumstances. If the wounds are chronic wounds, or if an object which caused the wound was dirty or contained bacteria, or from a bite, or contains remnant or a whole object that caused the wound, or a wound that is large or deep, or jagged edges to the wound, or elderly, or chronic because by their nature a wound site is open; and/or if the patient has: diabetes type 1 or type 2, is elderly, or has a compromised immune system.

Pressure gradient wound therapy may also be useful for treating second- and third-degree burns, as well as being useful for laparotomy surgery i.e., a large incision through an abdominal wall to gain access into the abdominal cavity.

In general, the invention relates to a pump assembly 10 and a pressure gradient wound therapy apparatus 50 comprising the pump assembly 10.

Figure 1:
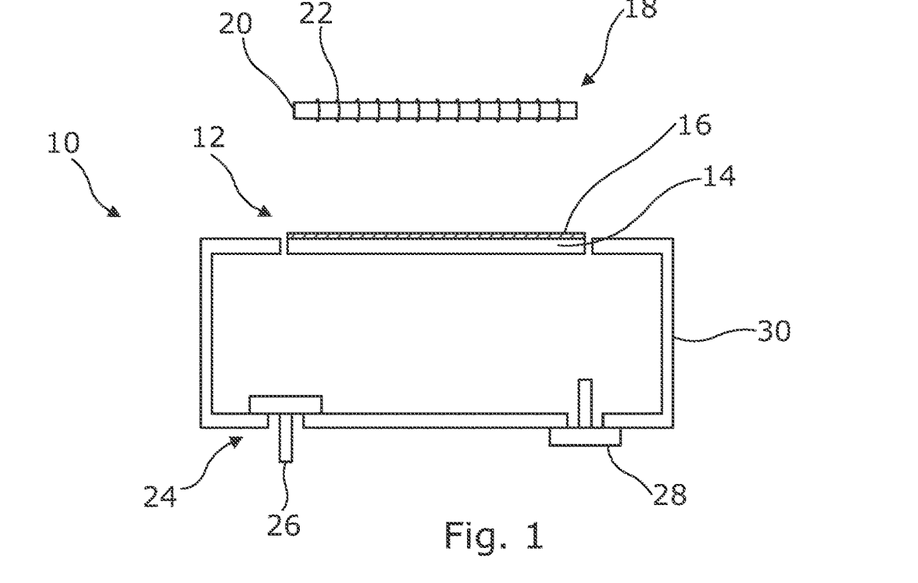
FIG. 1 is a schematic overview of an embodiment of a pump assembly of the invention.

FIG. 1 illustrates a first embodiment of a pump assembly 10. The pump assembly 10 includes a diaphragm 12, electromagnetic actuator 18 and valve arrangement 24. As discussed herein, the diaphragm 12 is configured to move under operation of the actuator 18 to control the introduction and/or removal of fluid into a fluid chamber 30. Specifically, the actuator 18 is configured in use to switch between two (or more) operational states, at least one of which corresponds to a state whereby the actuator 18 induces a magnetic field F1, F2 (FIGS. 2A, 2B) for controlling movement of the diaphragm 12. In this way, operation of the actuator 18 may be used to control the pressure inside a coupled wound dressing 52 (see FIG. 3).

The diaphragm 12 comprises a resilient member 14 which in this embodiment is circular and is fixed at its peripheral edge to the fluid chamber 30. As shown, in fixing the diaphragm 12 in this way, the resilient member 14 defines part of the wall of the fluid chamber 30 such that movement of the resilient member 14 in the manner described herein acts to increase or decrease the volume of the fluid chamber 30. The diaphragm 12 additionally includes a layer of magnetic material 16 applied to an outer surface of the resilient member 14. As discussed in detail herein, in use, the magnetic material 16 moves under the influence of an applied magnetic field F1, F2 (FIGS. 2A and 2B) causing the diaphragm 12 to flex between first and second positions to cause a pumping action.

Figure 2A:
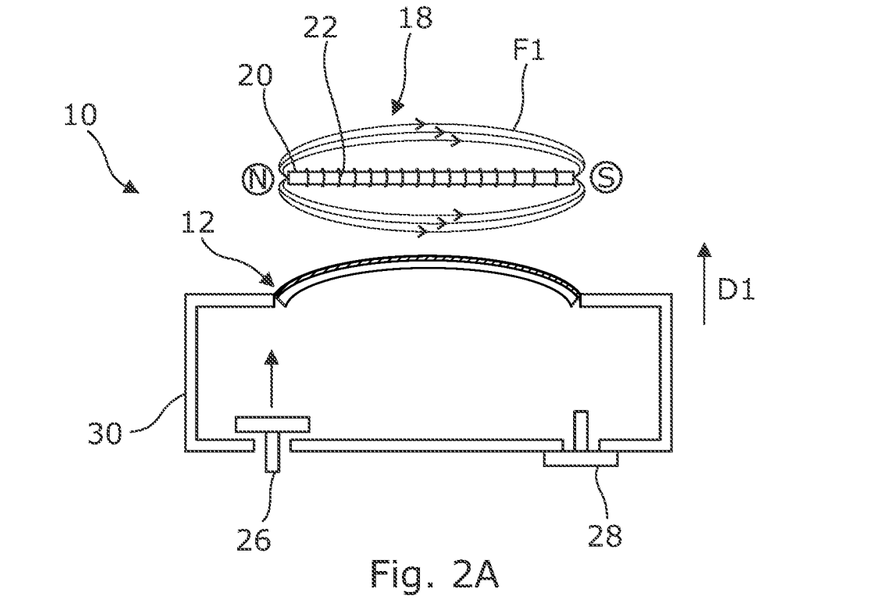
FIGS. 2A, 2B and 2C are schematic overviews of the pump assembly shown in FIG. 1 illustrating its operational use.
Figure 2B:
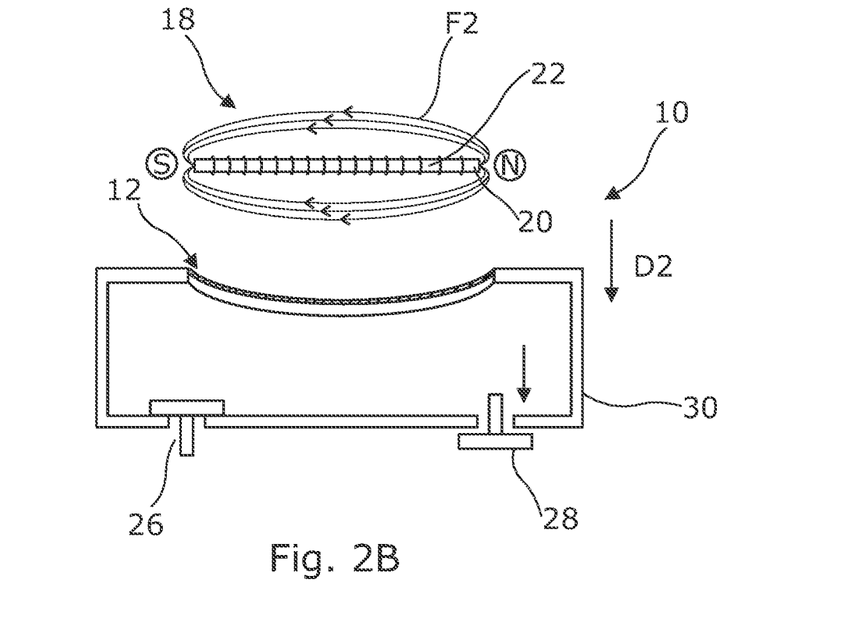
Figure 2C:
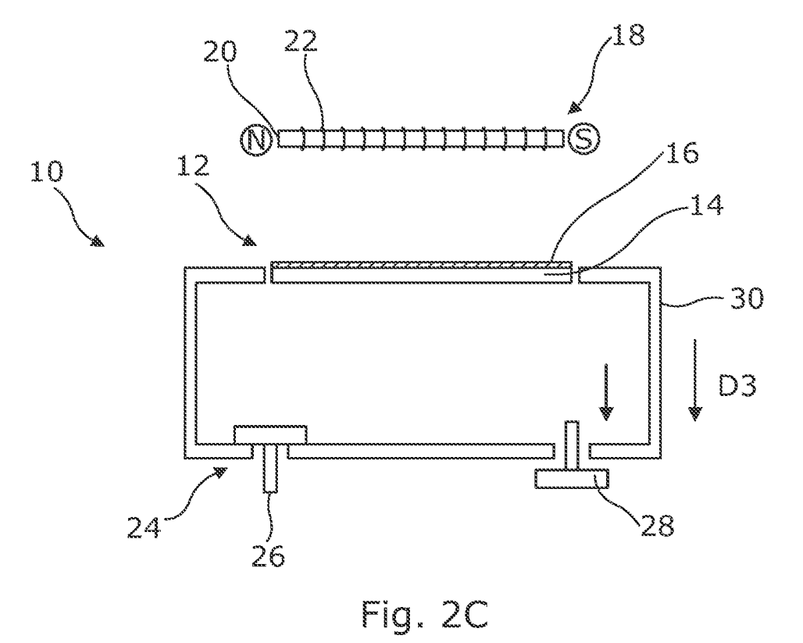

The actuator 18 comprises a wire coil 22 provided about a supporting member 20 that extends in a longitudinal direction. The supporting member 20 can be formed of any suitable material, and the invention is not limited in this sense. For instance, in embodiments the supporting member may comprise a magnetic material. Opposing ends of the coil 22 are electrically coupled to a power source (not shown) for controlling an electric current through the coil 22. In use, the direction of the electric current through the coil 22 determines the direction of the induced magnetic field. In the illustrated embodiment, the coil 22 is electrically coupled to a power source which in one embodiment may alternate the direction of current through the coil 22. In this way, the actuator 18 is configured to induce a magnetic field in two opposing directions, for instance field F1 in a first direction corresponding to a first operational state of the actuator 18, and field F2 in a second, opposing direction corresponding to a second operational state of the actuator 18 (as shown in FIGS. 2A and 2B respectively. In alternative embodiments the actuator 18 is configured to induce a magnetic field in one direction only. In such instances, the first operational state corresponds to a state where the magnetic field is "ON" (e.g. as shown in FIG. 2A) and the second operational state corresponds to a state where the magnetic field is "OFF" (e.g. as shown in FIG. 2C).

In use, the actuator 18 is advantageously fixed in position within the apparatus 50, at a set distance from the fluid chamber 30 and from the diaphragm 12 in its rest position. It is solely the movement of the diaphragm 12, flexing between first and second positions which causes the pumping action of pump assembly 10. This is in contrast to prior art devices wherein an electromagnetic actuator may be mounted to the diaphragm and may move through interaction with a permanent magnet provided about the actuator. Advantageously, reducing the number of moving components and reducing the size of the permanent magnet when compared with prior art devices inherently provides benefits in terms of efficiency and weight and size savings.

The valve arrangement 24 consists of an inlet valve 26 and an outlet valve 28. The opening and closing of the inlet valve 26 and outlet valve 28 is controlled via operation of the diaphragm 12 as described herein. As will be appreciated, the inlet valve 26 and outlet valve 28 comprise one-way valves.

In the illustrated arrangement, the inlet valve 26 is configured to allow only for the introduction of fluid, specifically gas withdrawn from a coupled wound dressing (e.g. wound dressing 52), into the fluid chamber 30 of the pump assembly 10. Similarly, the outlet valve 28 is configured to allow only for the removal of fluid (gas) from within the fluid chamber 30 into the environment. This configuration is suitable where the pump assembly 10 is for use in a negative pressure wound therapy apparatus. It will, however, be appreciated that the inlet valve 26 may instead be configured to allow introduction of gas into the fluid chamber 30 from the environment, and outlet valve may instead be fluidly coupled to a wound dressing (e.g. wound dressing 52) and be configured to allow gas from within the fluid chamber 30 to be provided to the wound dressing. This alternative arrangement is suitable for use in a positive pressure wound therapy apparatus.

FIGS. 2A, 2B and 2C illustrate the operational use of the pump assembly 10.

In the configuration shown in FIG. 2A, the actuator 18 is in a first operational state. Here, a current is induced in the wire coil 22 in a first direction inducing a first magnetic field F1 about the actuator 18. The direction of the field F1 is such that the magnetic layer 16 of the diaphragm 12 is attracted towards the actuator 18. In doing so, the diaphragm 12 as a whole is drawn in a first direction D1 (upwards in the orientation shown in the Figures). Due to the diaphragm 12 being fixed at its periphery, the diaphragm 12 adopts a concave shape, effectively increasing the volume of the fluid chamber 30. This increase in volume has the effect of reducing the pressure inside the fluid chamber 30 causing the inlet valve 26 to be opened and fluid to be drawn therethrough. As discussed herein, in the illustrated embodiment the inlet valve 26 is fluidly connected to a wound dressing 52 allowing for gas from within the wound dressing 52 to be withdrawn into the fluid chamber 30. At the same time, outlet valve 28 is held shut to ensure the only fluid entering the chamber 30 is gas being withdrawn from the wound dressing 52.

Turning to FIG. 2B, in one embodiment the actuator 18 is switched to a second operational state. In this state, the current through the wire coil 22 is reversed, thereby inducing a second magnetic field F2, opposite in orientation to field F1, to be induced about the actuator 18. The direction of the field F2 is such that the magnetic layer 16 of the diaphragm 12 is repelled in a direction away from the actuator 18. As a result, the diaphragm 12 is pushed in a second direction D2 (downwards in the orientation shown in the Figures). This causes the diaphragm to adopt a convex shape, effectively decreasing the volume of the fluid chamber 30. This, causes a substantial increase in the pressure inside the fluid chamber 30 causing the outlet valve 28 to open allowing fluid (i.e. the gas previously withdrawn from the wound dressing 52) to be expelled from the fluid chamber 30 into the surrounding environment. At the same time, the inlet valve 26 is held shut during the "downstroke" of the diaphragm 12 to prevent gas from re-entering the wound dressing 52.

The actuator 18 is periodically switched between these two operational modes to cause the pumping action of the diaphragm 12 to remove (or in embodiments introduce) gas from the coupled wound dressing 52 to obtain a desired pressure level within the dressing itself.

As outlined above, the same effect is achieved by an embodiment illustrated with respect to FIGS. 2A and 2C in which the actuator 18 is configured to induce a magnetic field in one direction only whereby the first operational state corresponds to a state where the magnetic field is "ON" and the second operational state corresponds to a state where the magnetic field is "OFF".

In this configuration, the actuator is configured to move the diaphragm in a first direction towards the first position under the influence of the magnetic field as shown in FIG. 2A. and the diaphragm moves in a second direction towards the second rest position of FIG. 2C in the absence of the magnetic field as a result of a biasing force provided by or applied to the diaphragm.

In this configuration, again, internal pressure is reduced on the upstroke illustrated in FIG. 2A, drawing fluid into the chamber 30 and when the current is no longer induced, the resilience of the diaphragm biases it towards the rest position of FIG. 2C, pushing it in direction D3 D2 (downwards in the orientation shown in the Figures)

This causes the diaphragm to adopt a flat shape, effectively decreasing the volume of the fluid chamber 30. This, causes an increase in the pressure inside the fluid chamber 30 causing the outlet valve 28 to open allowing fluid (i.e. the gas previously withdrawn from the wound dressing 52) to be expelled from the fluid chamber 30 into the surrounding environment. At the same time, the inlet valve 26 is held shut during the "downstroke" of the diaphragm 12 to prevent gas from re-entering the wound dressing 52.

It will be appreciated that a similar action could be achieved with reciprocation between the configurations of FIG. 2B and FIG. 2C, although in that case, unlike in FIG. 2C, the inlet valve 26 would open in the absence of the magnetic field, whilst the outlet valve 28 would close in the absence of a magnetic field.

Figure 3:
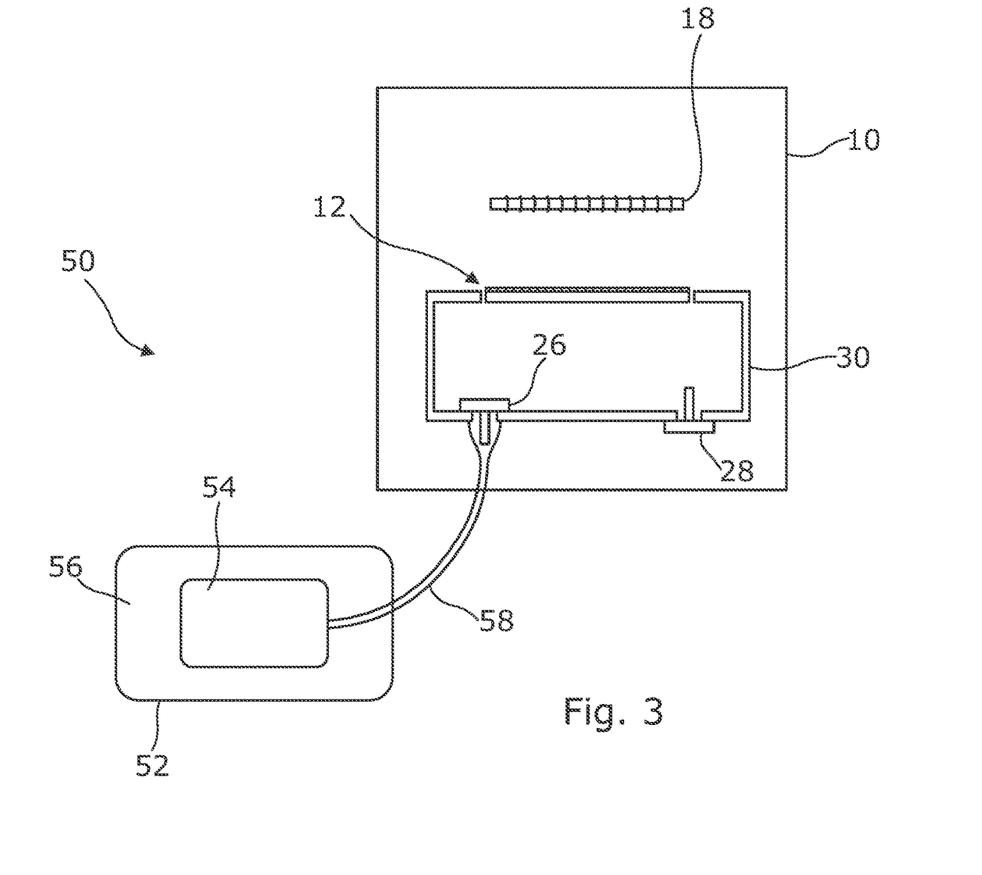
FIG. 3 is a schematic overview of an embodiment of a pressure gradient wound therapy apparatus of the invention.
Figure 4:
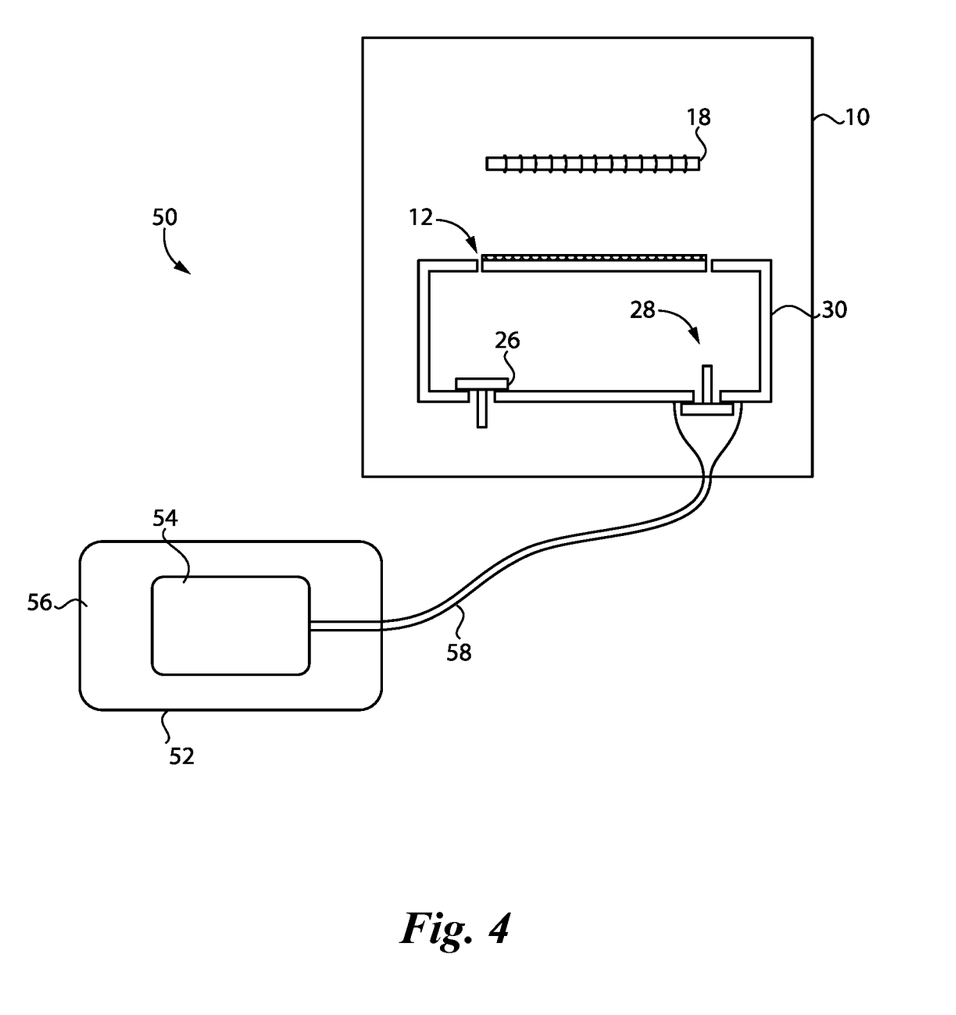
FIG. 4 is a schematic overview of an embodiment of a pressure gradient wound therapy apparatus.

FIG. 3 illustrates a pressure gradient wound therapy apparatus 50 in accordance with the invention. The apparatus 50 includes a wound dressing 52 which may, for example, be of the type available from ConvaTec Ltd. under the Avelle trade mark. The apparatus 50 additionally includes a pump assembly 10.

In the illustrated embodiment, the wound dressing 52 comprises a dressing body 54 and a peripheral adhesive layer 56. The dressing body 54 comprises an absorbent material and is positioned in contact with a wound, in use. The dressing body 54 is configured to absorb exudate from the wound, aided by the action of the pump assembly 10 creating a pressure differential between the interior of the wound dressing 52 and the surrounding environment. Here, the exudate is retained within the dressing body 54. Specifically, the dressing body 54 is formed of a hydrocolloid material which gels in the presence of exudate. This may be referred to as a "canister-less" system. In a variant, exudate removed from the wound may instead be withdrawn into an accompanying canister rather than being retained within the dressing body 54 itself. The exudate removed from the wound may be withdrawn into the accompanying canister via a conduit. The adhesive layer 56 provides a seal between the dressing 52 and the user's skin, in use, defining an interior region of the wound dressing 52 about the wound.

As discussed herein, the wound dressing 52 is fluidly connected to an inlet valve 26 of the pump assembly 10 via conduit 58 which may likewise be of the type available from ConvaTec Ltd. under the Avelle trade mark. In this arrangement, the pump assembly 10 is configured to withdraw air from the interior portion of the wound dressing 52 to reduce the pressure within the wound dressing 52 relative to the surrounding environment. Specifically, and as described herein, pump assembly 10 is configured to withdraw air from the wound dressing 52 via conduit 58 through inlet valve 26 into the fluid chamber 30. The withdrawn air is then expelled from the pump assembly 10 via outlet valve 28. This process is repeated until a sufficient amount of air has been removed from within the wound dressing 52 to achieve the desired pressure level therein.

In an alternative arrangement, the wound therapy apparatus 10 may comprise a positive pressure wound therapy apparatus 10. In such instances, the pump assembly 10 is configured to provide a source of air or other gas to be supplied to the interior portion of the wound dressing 52 to thereby increase the pressure within the wound dressing 52 relative to the surrounding environment. Specifically, the wound dressing 52 may instead be fluidly coupled to the outlet valve 28 of the pump assembly 10. Here, the pump assembly 10 is configured to withdraw air (or other gas) into the fluid chamber 30 from the surrounding environment or another source of gas through inlet valve 26 before expelling the withdrawn gas through outlet 28 and into the wound dressing 52 via conduit 58. This process may be repeated until a sufficient amount of air/gas has been introduced into the wound dressing 52 to achieve the desired pressure level therein.

Conditional language, such as "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without user input or prompting, whether these features, elements, and/or steps are included or are to be performed in any particular embodiment.

Each of the documents referred to above is incorporated herein by reference. Except in Examples, or where otherwise explicitly indicated, all numerical quantities in this description specifying amounts of materials, device dimension, and the like, are to be understood as modified by the word "about."

Unless otherwise indicated, each chemical or composition referred to herein should be interpreted as being a commercial grade material which may contain the isomers, by-products, derivatives, and other such materials which are normally understood to be present in the commercial grade. The one or more embodiments are described above by way of example only. Many variations are possible without departing from the scope of protection afforded by the appended claims.

The invention claimed is:

1. A pressure gradient wound therapy apparatus comprising a pump assembly, the pump assembly comprising:
   a diaphragm comprising a magnetic material, wherein the diaphragm has a resting position in which the diaphragm is planar and extends in a longitudinal direction;
   an electromagnetic actuator switchable between two or more operational states, at least one of which comprises a state in which the actuator induces a magnetic field for moving the diaphragm, wherein the electromagnetic actuator comprises a support that extends in the longitudinal direction and a coil wrapped about the support; and
   a valve arrangement including an inlet valve and an outlet valve configured to allow for introduction and/or removal of fluid into a fluid chamber of the pump assembly;
   wherein the electromagnetic actuator is fixed in position within the apparatus and is spatially separated from the diaphragm; and the electromagnetic actuator is configured to move the diaphragm with respect to the electromagnetic actuator between a first position corresponding to a first operational state of the electromagnetic actuator and a second position corresponding to a second operational state of the electromagnetic actuator; and
   wherein one of the inlet valve or the outlet valve is operable to be connected to a wound dressing via a conduit such that the pump assembly is operable to be positioned remotely relative to the wound dressing.

2. The pressure gradient wound therapy apparatus of claim 1, wherein the electromagnetic actuator is configured to move the diaphragm towards or away from the electromagnetic actuator when in the first or second operational state.

3. The pressure gradient wound therapy apparatus of claim 1, wherein in switching from the first operational state to the second operational state the electromagnetic actuator is configured to move the diaphragm in a first direction from the first position towards the second position, and in switching from the second operational state to the first operational state the electromagnetic actuator is configured to move the diaphragm in a second direction from the second position to the first position.

4. The pressure gradient wound therapy apparatus of claim 3, wherein the first direction is away from the electromagnetic actuator, and the second direction is towards the electromagnetic actuator.

5. The pressure gradient wound therapy apparatus of claim 1, wherein the electromagnetic actuator is operable to:
   induce a first magnetic field in the first operational state; and
   induce a second magnetic field in the second operational state.

6. The pressure gradient wound therapy apparatus of claim 1, wherein the electromagnetic actuator is operable to induce the magnetic field in the first operational state, only.

7. The pressure gradient wound therapy apparatus of claim 6, wherein the electromagnetic actuator is configured to move the diaphragm in a first direction towards the first position under the influence of the magnetic field; and
   wherein the electromagnetic actuator is configured such that the diaphragm moves in a second direction towards the second position in absence of the magnetic field.

8. The pressure gradient wound therapy apparatus of claim 7, wherein movement of the diaphragm in the second direction is provided by a biasing force provided by or applied to the diaphragm.

9. The pressure gradient wound therapy apparatus of claim 1, wherein the apparatus is configured such that a biasing force is provided which acts to bias the diaphragm to a resting position, wherein the resting position corresponds to the first position, the second position or an intermediary position between the first and second positions.

10. The pressure gradient wound therapy apparatus of claim 1, wherein the diaphragm is formed of a non-magnetic material comprising a magnetic component attached, coupled or otherwise fixed thereto.

11. The pressure gradient wound therapy apparatus of any claim 1, wherein the magnetic material of the diaphragm comprises a permanent magnetic material.

12. A pump assembly for a pressure gradient wound therapy apparatus, the pump assembly comprising:
   a diaphragm comprising a magnetic material, wherein the diaphragm has a resting position in which the diaphragm is planar and extends in a longitudinal direction;
   an electromagnetic actuator switchable between two or more operational states, at least one of which comprises a state in which the actuator induces a magnetic field for moving the diaphragm, wherein the electromagnetic actuator comprises a support that extends in the longitudinal direction and a coil wrapped about the support; and a valve arrangement including an inlet valve and an outlet valve configured to allow for introduction and/or removal of fluid into a fluid chamber of the pump assembly;

wherein the actuator, in use, is fixed in position within the apparatus and is spatially separated from the diaphragm; and the actuator is configured to move the diaphragm with respect to the actuator between a first position corresponding to a first operational state of the actuator and a second position corresponding to a second operational state of the actuator; and wherein the pump assembly is configured to be connected with a wound dressing via a conduit such that the pump assembly is operable to be positioned remotely from the wound dressing.

13. A pressure gradient wound therapy system, comprising:

a pump assembly, comprising:
a housing at least partially defining a fluid chamber;
a diaphragm comprising a magnetic material, wherein the diaphragm further defines the fluid chamber;
an electromagnetic actuator switchable between a first operational state and a second operational state to move the diaphragm between a first position corresponding to the first operational state and a second position corresponding to the second operational state, wherein the electromagnetic actuator induces a magnetic field in at least one of the first operational state or the second operational state;
an inlet valve mounted to the housing and configured to allow for introduction of fluid into the fluid chamber as the diaphragm moves from the first position to the second position; and
an outlet valve mounted to the housing and configured to allow for removal of fluid from the fluid chamber as the diaphragm moves from the second position to the first position; and a conduit having a first end and a second end spaced apart from the first end, wherein the first end is connected with one of the inlet valve or the outlet valve, and wherein the second end is configured for connection to a wound dressing to place the one of the inlet valve or the outlet valve in fluid communication with the wound dressing;

wherein the electromagnetic actuator comprises a support that extends in a longitudinal direction and a coil wrapped about the support; and wherein the diaphragm has a resting position in which the diaphragm is planar and extends in the longitudinal direction.

14. The pressure gradient wound therapy system of claim 13, further comprising the wound dressing;

wherein the second end of the conduit is connected to the wound dressing such that the one of the inlet valve or the outlet valve is in fluid communication with the wound dressing.

15. The pressure gradient wound therapy system of claim 13, wherein the electromagnetic actuator is spaced apart from the diaphragm and has a fixed position relative to the housing.

16. The pressure gradient wound therapy system of claim 13, wherein the electromagnetic actuator comprises a support that extends in a longitudinal direction and a coil wrapped about the support; and wherein the diaphragm has a resting position in which the diaphragm is planar and extends in the longitudinal direction.

17. The pressure gradient wound therapy system of claim 16, wherein the resting position is between the first position and the second position.

18. The pressure gradient wound therapy system of claim 13, wherein the pressure gradient wound therapy system has a first configuration in which the first end of the conduit is connected with the inlet valve such that the pump assembly is operable to provide a negative pressure to the wound dressing; and wherein the pressure gradient wound therapy system has a second configuration in which the first end of the conduit is connected with the outlet valve such that the pump assembly is operable to provide a positive pressure to the wound dressing.

* * * * *